(12) United States Patent
Fukase et al.

(10) Patent No.: US 8,237,336 B2
(45) Date of Patent: *Aug. 7, 2012

(54) ARRAY SCANNING TYPE ULTRASOUND PROBE

(75) Inventors: Hirokazu Fukase, Kanagawa (JP); Kouji Ooura, Kanagawa (JP)

(73) Assignee: Panasonic Corporation, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/303,333

(22) Filed: Nov. 23, 2011

(65) Prior Publication Data

US 2012/0060613 A1    Mar. 15, 2012

Related U.S. Application Data

(62) Division of application No. 12/670,329, filed as application No. PCT/JP2008/002059 on Jul. 31, 2008, now Pat. No. 8,084,922.

(30) Foreign Application Priority Data

Aug. 1, 2007  (JP) ................................. 2007-200490

(51) Int. Cl.
*H01L 41/08* (2006.01)
(52) U.S. Cl. ........................................ 310/334; 600/437
(58) Field of Classification Search .................. 310/334, 310/335, 322, 323, 336, 320; 367/155, 157; 600/437, 459; *H01L 41/09*
See application file for complete search history.

(56) References Cited

U.S. PATENT DOCUMENTS

| | | | |
|---|---|---|---|
| 5,638,822 A * | 6/1997 | Seyed-Bolorforosh et al. | 310/320 |
| 6,014,898 A * | 1/2000 | Finsterwald et al. | 310/334 |
| 6,117,083 A * | 9/2000 | Buck et al. | 600/459 |
| 8,084,922 B2 * | 12/2011 | Fukase et al. | 310/334 |
| 2007/0293762 A1 | 12/2007 | Sawada et al. | |

FOREIGN PATENT DOCUMENTS

| | | |
|---|---|---|
| JP | 57-188195 A | 11/1982 |
| JP | 11-317999 A | 11/1999 |
| JP | 2006-87464 A | 4/2006 |
| JP | 2006-122657 A | 5/2006 |

OTHER PUBLICATIONS

International Search Report for PCT/JP2008/002059, Oct. 21, 2008.

* cited by examiner

*Primary Examiner* — Thomas Dougherty
*Assistant Examiner* — Karen B Addison
(74) *Attorney, Agent, or Firm* — Pearne & Gordon LLP

(57) ABSTRACT

A technology is disclosed which provides an array scanning type ultrasound probe capable of preventing a diminution of ultrasound of a piezoelectric device at the time of transmission and at the time of reception due to its damage and thereby reducing a sensitivity deterioration of a diagnostic image. According to the technology, included are an electroacoustic conversion unit formed by arranging multiple piezoelectric devices and multiple acoustic matching layers in a predetermined direction, each of the multiple piezoelectric devices being an electroacoustic conversion device, the multiple acoustic matching layers being respectively stacked on the multiple piezoelectric devices; and a signal flexible board transferring electric signals to be transmitted to and received from the multiple piezoelectric devices. An incision passing through the multiple piezoelectric devices in respective thickness directions of the piezoelectric devices and extending into the corresponding acoustic matching layers stacked thereon is provided in parallel to the arrangement direction.

5 Claims, 7 Drawing Sheets

1/18 OF WAVELENGTH

3 μm

1/12 OF WAVELENGTH

4 μm

1/9 OF WAVELENGTH

6 μm

PRIOR ART

ARRAY SCANNING TYPE ULTRASOUND PROBE

This application is a division of U.S. patent application Ser. No. 12/670,329 filed Jan. 22, 2010, which is incorporated herein by reference in its entirety.

TECHNICAL FIELD

The present invention relates to an ultrasound probe capable of reducing characteristic deterioration due to damage of a piezoelectric device.

BACKGROUND ART

A conventionally known ultrasound probe is one in which a piezoelectric device, one or more acoustic matching layers, a first signal flexible board, a second signal flexible board, and a backing member are stacked on top of one another (e.g., see the following Patent Document 1).

FIG. 13 shows a cross-sectional perspective view of an ultrasound element portion (acoustic stack) 101 of an array scanning type ultrasound probe. The ultrasound element portion 101 includes the piezoelectric device 102 which is an electroacoustic conversion device made of PZT piezoelectric ceramic or the like, one or more acoustic matching layers 103, a first signal flexible board 104 which transfers electric signals to be transmitted to and received from the piezoelectric device 102, a second signal flexible board 105 which deals with electric signals of polarity opposite to that of the first signal flexible board 104, and a backing member 106 attached to the opposite side of the piezoelectric device 102 from the ultrasound emitting surface. The array scanning type ultrasound probe includes the ultrasound element portion 101, a housing (not shown) which covers the ultrasound element portion 101, a cable (not shown) for connection to an ultrasound diagnostic equipment (not shown), and the like.

In the ultrasound element portion 101, drive signals from the ultrasound diagnostic equipment (not shown) are applied to the piezoelectric device 102 through the first signal flexible board 104 and the second signal flexible board 105, converted into ultrasound signals by the piezoelectric device 102, and then applied to a subject (not shown) through the acoustic matching layers 103. Moreover, ultrasound signals reflected from the subject passes through the acoustic matching layers 103, and then are received and converted into electric signals by the piezoelectric device 102. The electric signals are sent to the ultrasound diagnostic equipment through the first signal flexible board 104 and the second signal flexible board 105 to undergo signal processing.

An ultrasound beam of the array scanning type ultrasound probe directed in the array (arrangement) direction (direction AA in the drawing) is formed into a desired beam shape to form a focal point at a predetermined depth, by controlling with the ultrasound diagnostic equipment several tens to several hundreds of individual elements 101a of the ultrasound element portion 101 which are divided in the array direction. Meanwhile, as to a direction (direction BB in the drawing, also expressed as the short axis direction) perpendicular to the array direction, an acoustic lens (not shown) which is generally made of silicone rubber or the like is used to form a focal point. This acoustic lens made of silicone rubber has frequency-dependent attenuation, and therefore deteriorates its sensitivity characteristics particularly when used in an array scanning type ultrasound probe using high frequencies. To address this, an array type ultrasound probe is known in which a flat piezoelectric device 102 is partly provided with incisions (kerfs) 107, and is mechanically curved with a certain curvature in the direction perpendicular to the array direction, thereby forming a focal point with the curvature instead of forming a beam shape by an acoustic lens.

Patent Document 1: Japanese Patent Application Publication H11-317999 (FIG. 1)

In the ultrasound element portion of the above-described conventional array scanning type ultrasound probe, the flat piezoelectric device 102 is partly provided with the incisions 107 and is mechanically curved with a certain curvature in the direction perpendicular to the array direction, thereby forming a focal point with the curvature. However, when mechanically curved, the piezoelectric device 102 made of ceramic or the like is apt to be cracked and damaged because stress concentrates at the regions of the incisions 107 of the piezoelectric device 102. This raises a problem that the damage reduces ultrasound of the array scanning type ultrasound probe at the time of transmission and reception, causing a sensitivity deterioration of a diagnostic image.

DISCLOSURE OF THE INVENTION

The present invention has been made to solve the above-described conventional problems. Multiple incisions are provided at regular intervals in a direction perpendicular to the array direction, each of the incisions being provided to pass through a piezoelectric device in the thickness direction and to extend to near a surface of an acoustic matching layer, the surface not being in contact with the piezoelectric device. In other words, the provision of the incisions passing through the piezoelectric device in the thickness direction mitigates stress concentration when the piezoelectric device is curved, thus making it possible to prevent the piezoelectric device from being damaged.

In the above-mentioned way, according to the present invention, an array scanning type ultrasound probe can be provided in which a sensitivity deterioration of a diagnostic image due to the damage of a piezoelectric device can be reduced and in which a curvature can favorably be formed in a direction perpendicular to the array direction.

To solve the above-described conventional problems, an ultrasound probe according to the present invention includes an electroacoustic conversion unit formed by arranging a plurality of piezoelectric devices and a plurality of acoustic matching layers in a predetermined direction, each of the plurality of piezoelectric devices being an electroacoustic conversion device, the plurality of acoustic matching layers being respectively stacked on the respective piezoelectric devices; and a signal flexible board transferring electric signals to be transmitted to and received from the plurality of piezoelectric devices, the ultrasound probe having a configuration in which an incision passing through the plurality of piezoelectric devices in respective thickness directions of the piezoelectric devices and extending into the corresponding acoustic matching layers stacked on the respective piezoelectric devices is provided in parallel to the arrangement direction.

This configuration can prevent a diminution of ultrasound at the time of transmission and at the time of reception due to the damage of a piezoelectric device. In other words, a sensitivity deterioration of a diagnostic image can be reduced.

Further, the ultrasound probe according to the present invention includes the incision provided in plurality at regular intervals in a direction perpendicular to the arrangement direction.

With this configuration, since a plurality of incisions are provided to reach the acoustic matching layers, the flexibility in shape of the acoustic matching layers are improved in the direction perpendicular to the array (arrangement) direction, and the acoustic matching layers can flexibly follow the curving of the piezoelectric device.

Further, the ultrasound probe according to the present invention has a configuration in which the acoustic matching layers are longer in length in the direction perpendicular to the arrangement direction than the piezoelectric devices.

Compared to the case where the lengths of the acoustic matching layers and the piezoelectric devices are the same, this configuration can prevent disturbance in ultrasound at end portions of the piezoelectric devices, and can prevent a diminution of ultrasound transmission and reception signal due to the damage of a piezoelectric device at the time of fabrication. In other words, a sensitivity deterioration of a diagnostic image can be reduced.

Further, the ultrasound probe according to the present invention has a configuration in which, in the acoustic matching layers stacked on the piezoelectric devices, an incision is provided in a portion of the acoustic matching layers, the portion protruding from the piezoelectric devices.

This configuration prevents an inflection point in a cross-sectional shape at the end portions of the piezoelectric devices from being caused by the distortion of the acoustic matching layers, and prevents stress from concentrating at the end portions of the piezoelectric devices, thereby capable of reducing a sensitivity deterioration of a diagnostic image caused by the damage of a piezoelectric device.

Further, in the ultrasound probe according to the present invention, the incision in the acoustic matching layers is provided to have such a depth that the remaining acoustic matching layers have a dimension of less than ⅕ of a wavelength of ultrasound emitted by the piezoelectric devices.

This configuration makes it possible to reduce the thickness of junction points left after making the incision in the acoustic matching layers, thus improving flexibility when the acoustic matching layers are formed into curved shapes. Accordingly, a sensitivity deterioration of a diagnostic image due to the damage of a piezoelectric device can be reduced, and a curvature can favorably be formed in the direction perpendicular to the array direction.

The present invention can prevent a diminution of ultrasound at the time of transmission and at the time of reception due to the damage of a piezoelectric device, by providing incisions at regular intervals in the direction perpendicular to the array direction, the incisions passing through the piezoelectric devices in the thickness direction and extending to near the surfaces of the acoustic matching layers which are not in contact with the piezoelectric devices. In other words, an array scanning type ultrasound probe can be provided which has the effect of reducing a sensitivity deterioration of a diagnostic image.

BEST MODE FOR CARRYING OUT THE INVENTION

Hereinafter, an array scanning type ultrasound probe of an embodiment of the present invention will be described with reference to the drawings.

First Embodiment

Figure 1:
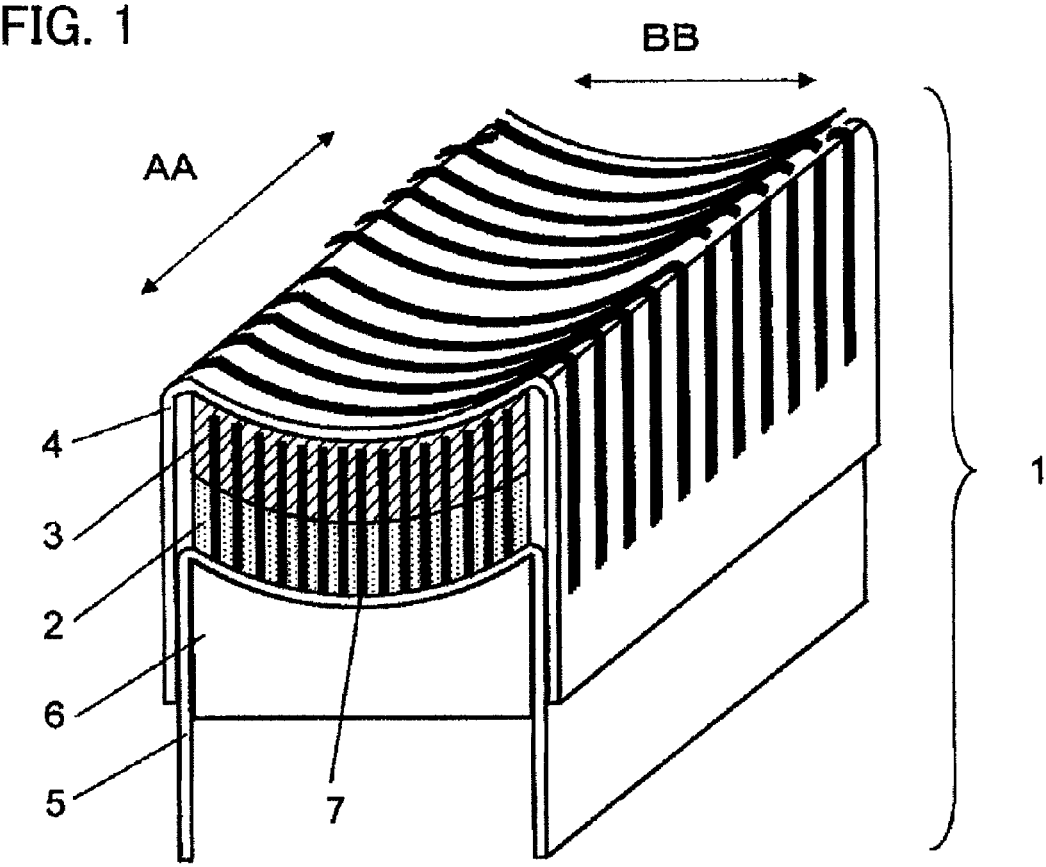
FIG. 1 A cross-sectional perspective view of a first embodiment of the present invention.

FIG. 1 shows a cross-sectional perspective view of a plane perpendicular to the array (arrangement) direction (direction AA in the drawing) of an ultrasound element portion 1 of an ultrasound probe of a first embodiment of the present invention (plane containing direction BB in the drawing, also expressed as the short axis direction).

As shown in FIG. 1, the ultrasound element portion 1 which transmits and receives ultrasound includes an electroacoustic conversion unit, a first signal flexible board 4, a second signal flexible board 5, and a backing member 6. The electroacoustic conversion unit includes a piezoelectric device 2 and an acoustic matching layer 3. The piezoelectric device 2 is made of piezoelectric ceramic such as PZT ceramic or the like and transmits and receives ultrasound. The acoustic matching layer 3 is used to allow ultrasound to efficiently propagate and made of resin containing added electrically conductive material or graphite. The first signal flexible board 4 transfers electric signals to be transmitted to and received from the piezoelectric device 2. The second signal flexible board 5 deals with electric signals of polarity opposite to that of the first signal flexible board 4. The backing member 6 mechanically holds the piezoelectric device 2 and has the function of attenuating unnecessary ultrasound signals. The first signal flexible board 4, the acoustic matching layer 3, the piezoelectric device 2, the second signal flexible board 5, and the backing member 6 are stacked in this order. It should be noted that electrodes are provided on two surfaces of the piezoelectric device 2, the surfaces being opposite to each other in the stacking direction.

Specifically, this ultrasound element portion 1 is divided into several tens to several hundreds of elements in the array direction and divided into several tens of elements in the short axis direction by making incisions by means of cutting (dicing) or the like not only in the short axis direction (BB) at regular intervals but also in the array direction (AA) at regular intervals.

The ultrasound element portion 1 configured as described above generates ultrasound by exerting the electroacoustic conversion effect of the piezoelectric device 2 on a starting voltage which is applied from an ultrasound diagnostic equipment (not shown) through the first signal flexible board 4 and the second signal flexible board 5, and applies the ultrasound to a subject (not shown) through the acoustic matching layer 3. Moreover, the ultrasound reflected from the subject passes through the acoustic matching layer 3 to be received by the piezoelectric device 2 and converted into electric signals by the electroacoustic conversion effect of the piezoelectric device 2, taken out by the first signal flexible board 4 and the second signal flexible board 5, and computed by the ultrasound diagnostic equipment. It should be noted that though the acoustic matching layer 3 is stacked between the piezoelectric device 2 and the first signal flexible board 4, the acoustic matching layer 3 is made of resin, graphite, or the like containing electrically conductive material and therefore allows electric signals to be transferred between the piezoelectric device 2 and the first signal flexible board 4.

Here, as to an ultrasound beam in the array direction, by delaying the transmission or reception times of signals from the ultrasound diagnostic equipment to the several tens to several hundreds of divided elements, an ultrasound beam in which ultrasound signals from the respective elements are combined together is produced. As to an ultrasound beam in the direction perpendicular to the array direction, an ultrasound beam is produced by curving the ultrasound element portion 1 to a desired curvature in the direction perpendicular to the array direction. A favorable ultrasound image is extracted by a combination of the ultrasound beam in the array direction and the ultrasound beam in the direction perpendicular to the array direction.

Next, a preferred fabrication process of the array scanning type ultrasound probe operating in this way will be described.

Figure 2:
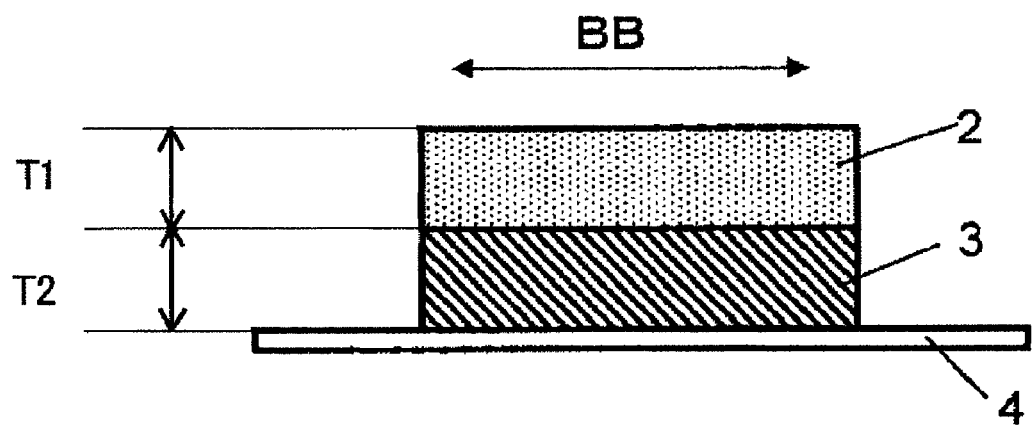
FIG. 2 A cross-sectional view of a stack of a piezoelectric device, an acoustic matching layer, and a signal flexible board.

FIG. 2 shows a cross-sectional view of a stacked state as seen from the direction perpendicular to the array direction. The piezoelectric device 2, the acoustic matching layer 3, and the first signal flexible board 4 are bonded together using an epoxy adhesive or the like to be stacked in this order. Here, at the time of bonding using an epoxy adhesive or the like, ohmic contacts can be respectively formed between the piezoelectric device 2 and the acoustic matching layer 3 and between the acoustic matching layer 3 and the first signal flexible board 4 by extremely thinning adhesive layers. Thus, electrical connections among the piezoelectric device 2, the acoustic matching layer 3, and the first signal flexible board 4 can be obtained.

In FIG. 2, the several to several tens of incisions 7 are provided in parallel to the array direction at an equal pitch approximately 0.6 times the thickness of the piezoelectric device 2 by means of cutting or the like so that the incisions 7 can pass through the piezoelectric device 2 in the thickness direction and extend to near the surface of the acoustic matching layer 3, the surface not being in contact with the piezoelectric device 2. In other words, the incisions are provided from the piezoelectric device 2 side to the acoustic matching layer 3 side with a dimension (T3) equal to or greater than the thickness dimension (T1) of the piezoelectric device and less than the value obtained by adding the thickness dimension (T2) of the acoustic matching layer to the thickness dimension (T1) of the piezoelectric device.

Figure 3:
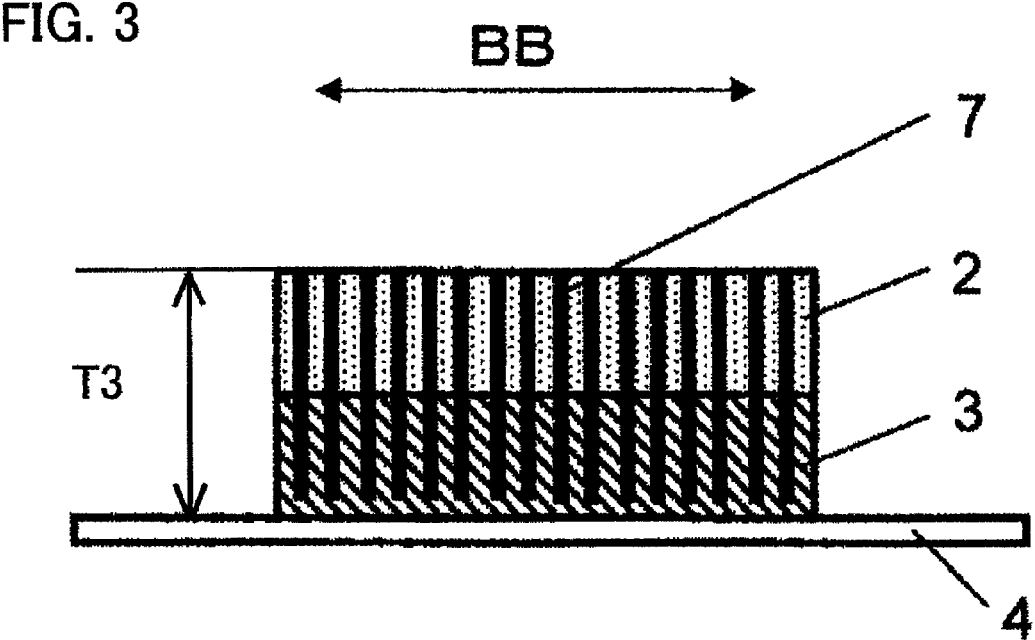
FIG. 3 A cross-sectional view showing incisions provided in parallel to an array direction after stacking the piezoelectric device, the acoustic matching layer, and the signal flexible board together.

Here, when the incisions 7 are provided by means of cutting or the like, the incisions are made to extend to near the surface of the acoustic matching layer 3, the surface not being in contact with the piezoelectric device 2, so that the piezoelectric device 2 and the acoustic matching layer 3 may not break up. FIG. 3 shows a cross-sectional view of a state in which incisions are made, as seen from the direction perpendicular to the array direction.

In FIG. 1, a stack of the first signal flexible board 4, the acoustic matching layer 3, the piezoelectric device 2, the second signal flexible board 5, and the backing member 6 is shown; in FIGS. 2 and 3, a stack of the first signal flexible board 4, the acoustic matching layer 3, and the piezoelectric device 2 is shown. However, a plurality of acoustic matching layers 3 may be stacked between the piezoelectric device 2 and the first signal flexible board 4.

Next, the backing member 6 and the second signal flexible board 5 which have been given a desired curvature beforehand are bonded to the unit of FIG. 3 using an epoxy adhesive or the like to be stacked thereon. At this time, it should be ensured that the incisions 7 are filled with the adhesive. Here, at the time of bonding using an epoxy adhesive or the like, an ohmic contact can be formed between the piezoelectric device 2 and the second signal flexible board 5 by extremely thinning the adhesive layer. Thus, an electrical connection between the piezoelectric device 2 and the second signal flexible board 5 can be obtained.

Figure 4:
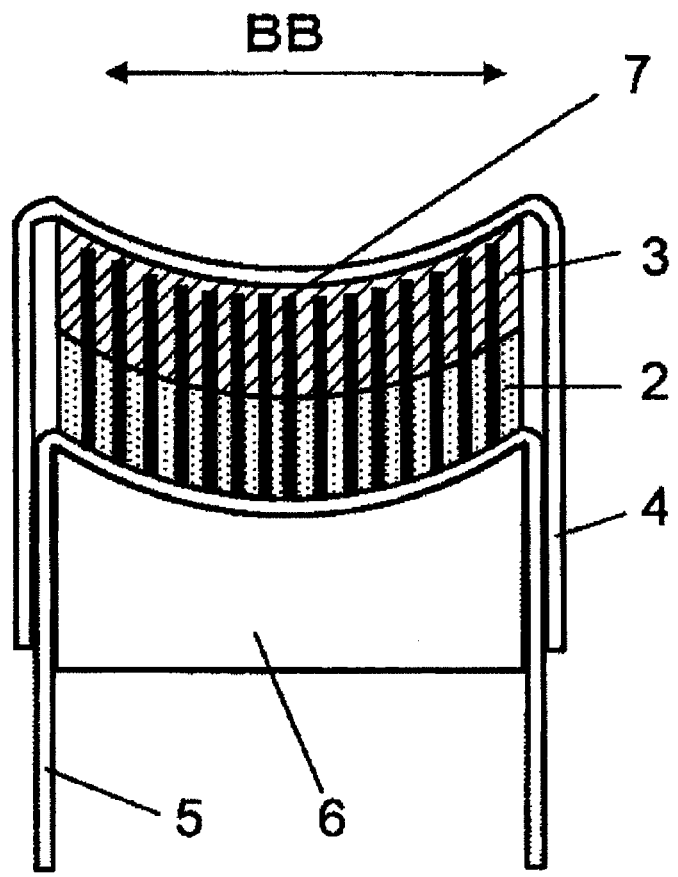
FIG. 4 A cross-sectional view of the first embodiment of the present invention as seen from a direction perpendicular to the array direction.

FIG. 4 shows a cross-sectional view of this state as seen from the direction perpendicular to the array direction. At this time, a favorable shape can be held by performing bonding while applying pressure from the surface, of the piezoelectric device 2, which is on the side of the first signal flexible board 4 in FIG. 3 using a supporting tool (not shown) which has a curvature approximately the same as the curvature preformed in the backing member 6.

The unit of FIG. 4 is further divided into several tens to several hundreds of elements in the direction perpendicular to the array direction by means of cutting or the like. Thus, the ultrasound element portion 1 of FIG. 1 is completed. At this time, since the incisions 7 have an anchor effect to improve the adhesive strength of the unit of FIG. 4, division by cutting is favorably performed.

At the time of forming the unit of FIG. 3 into the unit of FIG. 4, the above-described means prevents stress concentration at the piezoelectric device 2 from being caused by mechanically curving the unit of FIG. 3 so that the unit of FIG. 3 may have a curvature in the direction perpendicular to the array direction, and eliminates the risk that the piezoelectric device 2 will be damaged, since the incisions 7 passing through the piezoelectric device 2 are provided at regular intervals in the direction perpendicular to the array direction.

It should be noted that though an array type ultrasound probe with a linear shape has been described in this embodiment, similar effects are also exerted on a convex type of array type ultrasound probe in the shape of a sector.

From the above, the use of the array type ultrasound probe of this embodiment can prevent a diminution of ultrasound at the time of transmission and at the time of reception due to the damage of a piezoelectric device. In other words, a sensitivity deterioration of a diagnostic image can be reduced.

Second Embodiment

Figure 5:
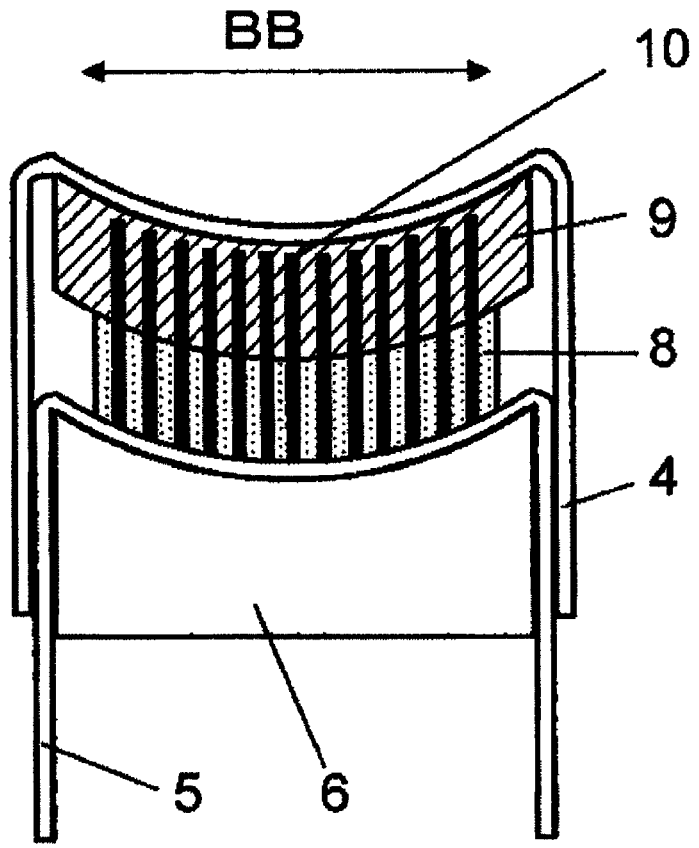
FIG. 5 A cross-sectional view of a second embodiment of the present invention as seen from a direction perpendicular to the array direction.

FIG. 5 shows a cross-sectional view of an ultrasound element portion of a second embodiment of the present invention as seen from the direction perpendicular to the array direction.

FIG. 5 shows a configuration in which a piezoelectric device 8 is shorter in length in the direction perpendicular to the array direction than components of an acoustic matching layer 9 and the backing member 6 (the dimension of the acoustic matching layer in the short axis direction is longer than the dimension of the piezoelectric device in the short axis direction).

Figure 6:
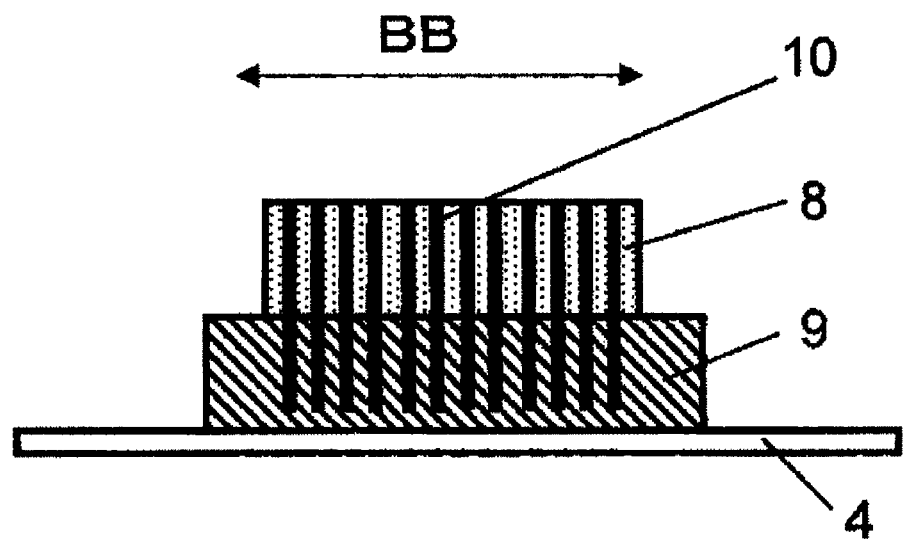
FIG. 6 A cross-sectional view of the second embodiment of the present invention in a state in which incisions are provided in parallel to the array direction.

In the ultrasound element portion of FIG. 5, the piezoelectric device 8, the acoustic matching layer 9, and the first signal flexible board 4 are bonded together using an epoxy adhesive or the like to be stacked in this order. At this time, it is desirable that the piezoelectric device 8 be located on a middle portion relative to the acoustic matching layer 9 in the direction perpendicular to the array direction. FIG. 6 shows a cross-sectional view as seen from the direction perpendicular to the array direction in the stage in which incisions have been made. Incisions 10 are provided in parallel to the array direction at an equal pitch approximately 0.6 times the length of the piezoelectric device 8 in the thickness direction. Specifically, several to several tens of incisions 10 are provided by means of cutting or the like so as to pass through the piezoelectric device 8 in the thickness direction to extend to near the surface of the acoustic matching layer 9, the surface not being in contact with the piezoelectric device 8. Here, when the incisions 10 are provided by means of cutting or the like, incisions are made to extend to near the surface of the acoustic matching layer 9, the surface not being in contact with the piezoelectric device 8, so that the piezoelectric device 8 and the acoustic matching layer 9 may not break up. Meanwhile, at this time, in portions of the acoustic matching layer 9 which are not in contact with the piezoelectric device 8, the incisions 10 are not provided by means of cutting or the like.

In FIG. 5, a stack of the first signal flexible board 4, the acoustic matching layer 9, the piezoelectric device 8, the second signal flexible board 5, and the backing member 6 is shown; in FIG. 6, a stack of the first signal flexible board 4, the acoustic matching layer 9, and the piezoelectric device 8 is shown. However, a plurality of acoustic matching layers 9 may be stacked between the piezoelectric device 8 and the first signal flexible board 4.

The backing member 6 and the second signal flexible board 5 which have been given a desired curvature beforehand are bonded to the unit of FIG. 6 using an epoxy adhesive or the like to be stacked thereon, thus making the configuration of FIG. 5. At this time, it should be ensured that the incisions 10 are filled with the adhesive.

After that, division into several tens to several hundreds of elements is performed in the direction perpendicular to the array direction by means of cutting or the like. At this time, since the incisions 10 have an anchor effect to improve the adhesive strength of the unit of FIG. 5, division by cutting is favorably performed.

The above-described means prevents stress concentration at the piezoelectric device 8 from being caused by mechanically curving the unit of FIG. 6 so that the unit of FIG. 6 may have a curvature in the direction perpendicular to the array direction, and eliminates the risk that the piezoelectric device 8 will be damaged, since the incisions 10 passing through the piezoelectric device 8 are provided at regular intervals in the direction perpendicular to the array direction.

It should be noted that this embodiment also has similar effects on an array type ultrasound probe with a linear shape and a convex type of array type ultrasound probe in the shape of a sector.

From the above, the use of the array type ultrasound probe of this embodiment can prevent a diminution of ultrasound at the time of transmission and at the time of reception due to the damage of a piezoelectric device. In other words, a sensitivity deterioration of a diagnostic image can be reduced.

Third Embodiment

Figure 7:
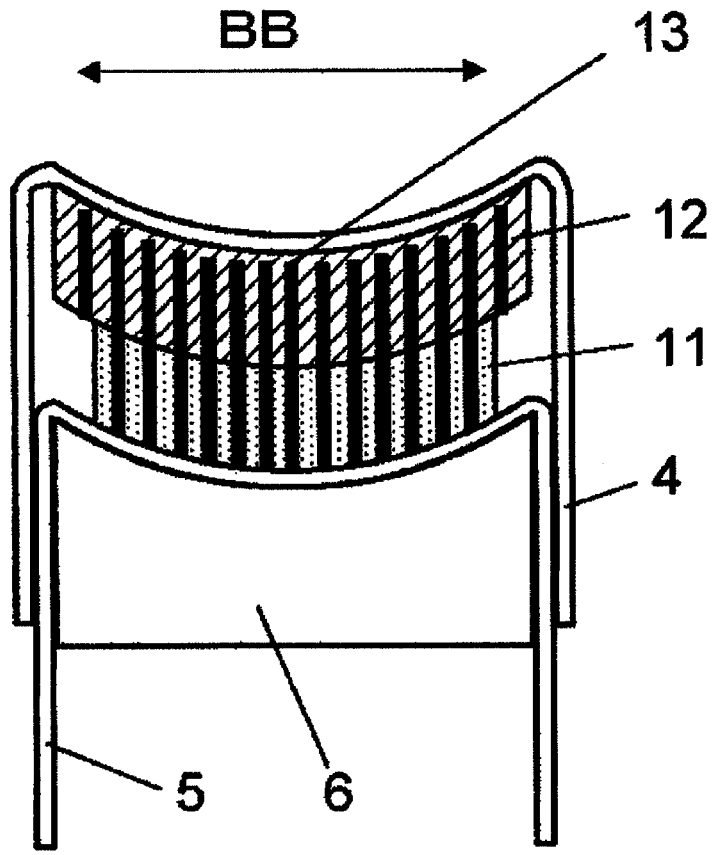
FIG. 7 A cross-sectional view of a third embodiment of the present invention as seen from a direction perpendicular to the array direction.

FIG. 7 shows a cross-sectional view of an ultrasound element portion of a third embodiment of the present invention as seen from the direction perpendicular to the array direction.

FIG. 7 shows a configuration in which a piezoelectric device 11 is shorter in length in the direction perpendicular to the array direction than components of an acoustic matching layer 12 and the backing member 6 as the case of FIG. 5.

Figure 8:
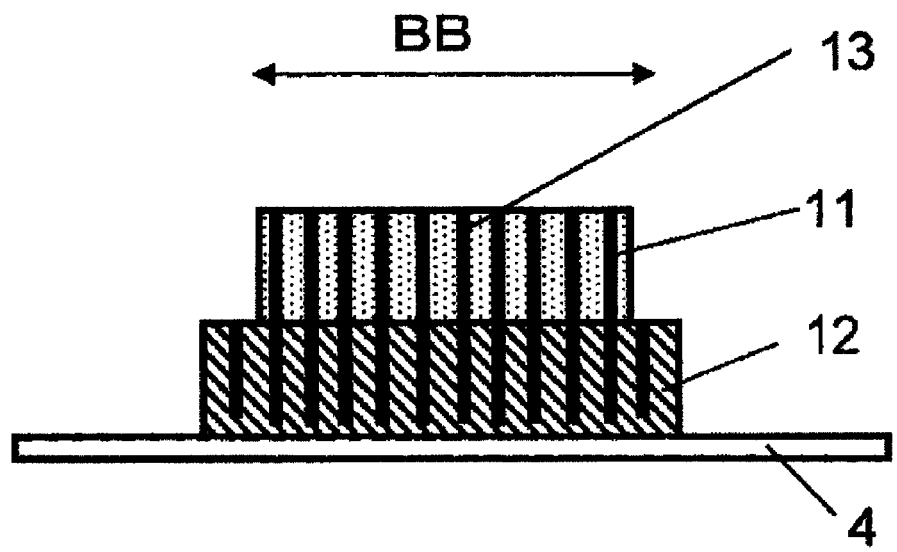
FIG. 8 A cross-sectional view of the third embodiment of the present invention in a state in which incisions are provided in parallel to the array direction.

In the ultrasound element portion of FIG. 7, the piezoelectric device 11, the acoustic matching layer 12, and the first signal flexible board 4 are bonded together using an epoxy adhesive or the like to be stacked in this order. At this time, it is desirable that the piezoelectric device 11 be located on a middle portion relative to the acoustic matching layer 12 in the direction perpendicular to the array direction. FIG. 8 shows a cross-sectional view as seen from the direction perpendicular to the array direction in the stage in which incisions have been made. Several to several tens of incisions 13 are provided in parallel to the array direction at an equal pitch approximately 0.6 times the length of the piezoelectric device 11 in the thickness direction by means of cutting or the like so as to pass through the piezoelectric device 11 in the thickness direction to extend to near the surface of the acoustic matching layer 12, the surface not being in contact with the piezoelectric device 11. Here, when the incisions 13 are provided by means of cutting or the like, incisions are made to extend to near the surface of the acoustic matching layer 12, the surface not being in contact with the piezoelectric device 11, so that the piezoelectric device 11 and the acoustic matching layer 12 may not break up. Moreover, at this time, in portions of the acoustic matching layer 12 which are not in contact with the piezoelectric device 11, the incisions 13 are also provided similarly.

In FIG. 7, a stack of the first signal flexible board 4, the acoustic matching layer 12, the piezoelectric device 11, the second signal flexible board 5, and the backing member 6 is shown; in FIG. 8, a stack of the first signal flexible board 4, the acoustic matching layer 12, and the piezoelectric device 11 is shown. However, a plurality of acoustic matching layers 12 may be stacked between the piezoelectric device 11 and the first signal flexible board 4.

The backing member 6 and the second signal flexible board 5 which have been given a desired curvature beforehand are bonded to the unit of FIG. 8 using an epoxy adhesive or the like to be stacked thereon, thus making the configuration of FIG. 7.

After that, division into several tens to several hundreds of elements is performed in the direction perpendicular to the array direction by means of cutting or the like. At this time, since the incisions 10 have an anchor effect to improve the adhesive strength of the unit of FIG. 5, division by cutting is favorably performed.

The above-described means prevents stress concentration at the piezoelectric device 11 from being caused by mechanically curving the unit of FIG. 8 so that the unit of FIG. 8 may have a curvature in the direction perpendicular to the array direction, and eliminates the risk that the piezoelectric device 11 will be damaged, since the incisions 13 passing through the piezoelectric device 11 are provided at regular intervals in the direction perpendicular to the array direction.

It should be noted that this embodiment also has similar effects on an array type ultrasound probe with a linear shape and a convex type of array type ultrasound probe in the shape of a sector.

From the above, the use of the ultrasound probe of this embodiment can prevent a diminution of ultrasound at the time of transmission and at the time of reception due to the damage of a piezoelectric device. In other words, a sensitivity deterioration of a diagnostic image can be reduced.

Fourth Embodiment

Figure 9:
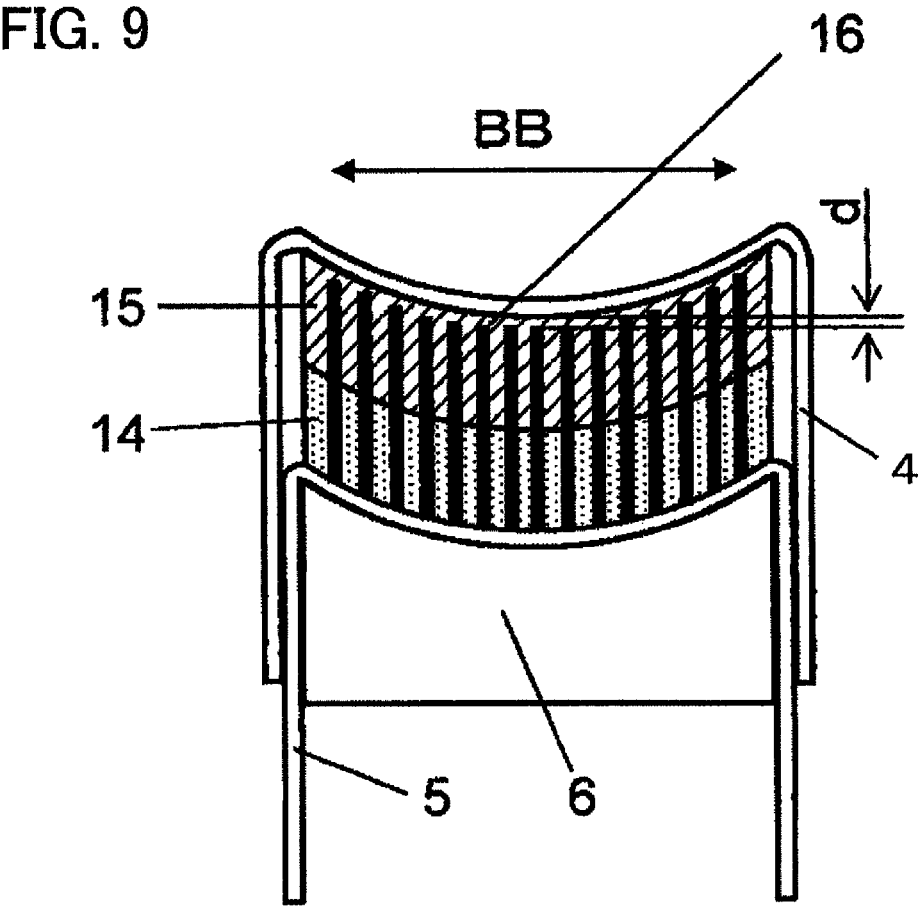
FIG. 9 A cross-sectional view of a fourth embodiment of the present invention as seen from a direction perpendicular to the array direction.

FIG. 9 shows a cross-sectional view of an ultrasound element portion of a fourth embodiment of the present invention as seen from the direction perpendicular to the array direction.

In FIG. 9, an acoustic matching layer 15 is provided with incisions 16 at regular intervals in the direction perpendicular to the array direction with a thickness (d in the same drawing) less than 1/9 of the wavelength of the ultrasound emitted by a piezoelectric device 15 being left in the thickness direction from the surface, of the acoustic matching layer 15, the surface not being in contact with the piezoelectric device 14.

Figure 10:
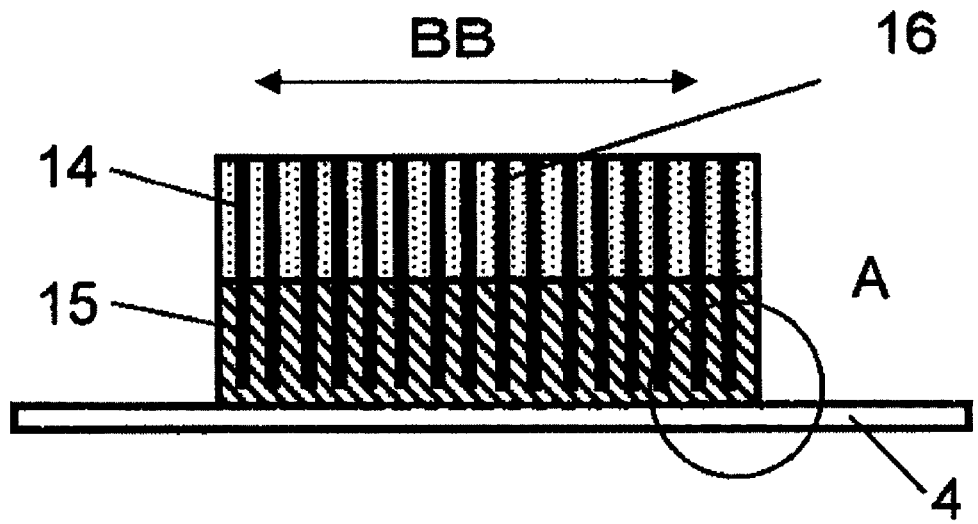
FIG. 10 A cross-sectional view of the fourth embodiment of the present invention in a state in which incisions are provided in parallel to the array direction.
Figure 11:
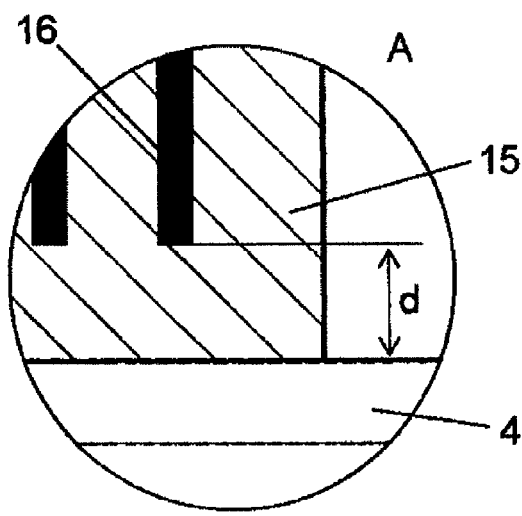
FIG. 11 An enlarged view of part A of the cross-sectional view of the fourth embodiment of the present invention in a state in which incisions are provided in parallel to the array direction.

In the ultrasound element portion of FIG. 9, the piezoelectric device 14, the acoustic matching layer 15, and the first signal flexible board 4 are bonded together using an epoxy adhesive or the like to be stacked in this order. FIG. 10 shows a cross-sectional view as seen from the direction perpendicular to the array direction in the fabrication process, and FIG. 11 shows an enlarged view of part A of FIG. 10 in which a thickness less than 1/9 of the wavelength is left in the acoustic matching layer 15 in the thickness direction from the surface of the acoustic matching layer 15, the surface not being in contact with the piezoelectric device 14. Specifically, several to several tens of incisions 16 are provided in parallel to the array direction at an equal pitch approximately 0.6 times the length of the piezoelectric device 14 in the thickness direction by means of cutting or the like so as to cut through the piezoelectric device 14 in the thickness direction with a thickness less than 1/9 of the wavelength being left in the thickness direction from the surface of the acoustic matching layer 15, the surface not being in contact with the piezoelectric device 14. Here, when the incisions 16 are provided by means of cutting or the like, a thickness less than 1/9 of the wavelength is left in the acoustic matching layer 15 in the thickness direction from the surface of the acoustic matching layer 15, the surface not being in contact with the piezoelectric device 14 so that the piezoelectric device 14 and the acoustic matching layer 15 may not break up. Moreover, a uniform curvature can be formed in the direction perpendicular to the array direction by leaving a thickness (d in FIG. 11) less than 1/9 of the wavelength in the acoustic matching layer 15 from the surface thereof which is not in contact with the piezoelectric device 14.

In FIG. 9, a stack of the first signal flexible board 4, the acoustic matching layer 15, the piezoelectric device 14, the second signal flexible board 5, and the backing member 6 is shown; in FIG. 10, a stack of the first signal flexible board 4, the acoustic matching layer 15, and the piezoelectric device 14 is shown. However, a plurality of acoustic matching layers 15 may be stacked between the piezoelectric device 14 and the first signal flexible board 4.

Figure 12:
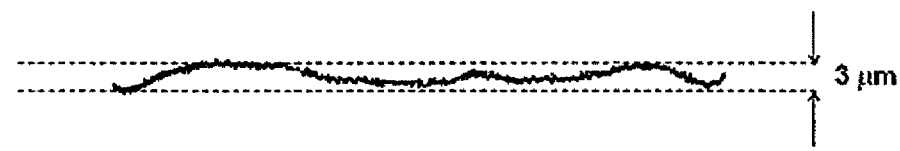
FIG. 12 A characteristic data view obtained by measuring a radius of curvature in direction BB of FIG. 9.
Figure 12:
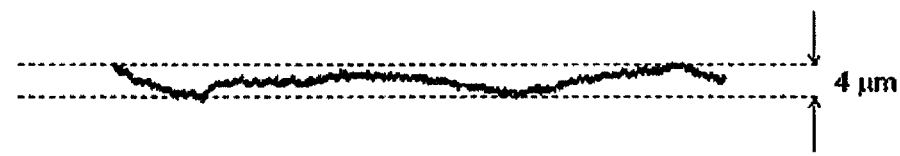
Figure 12:
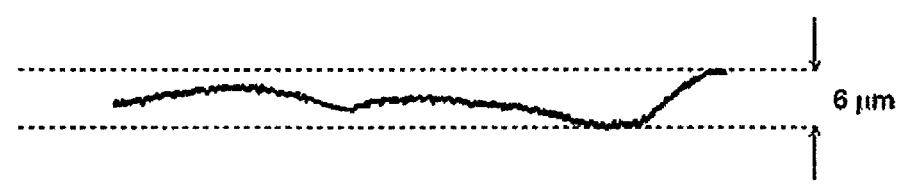
Figure 13:
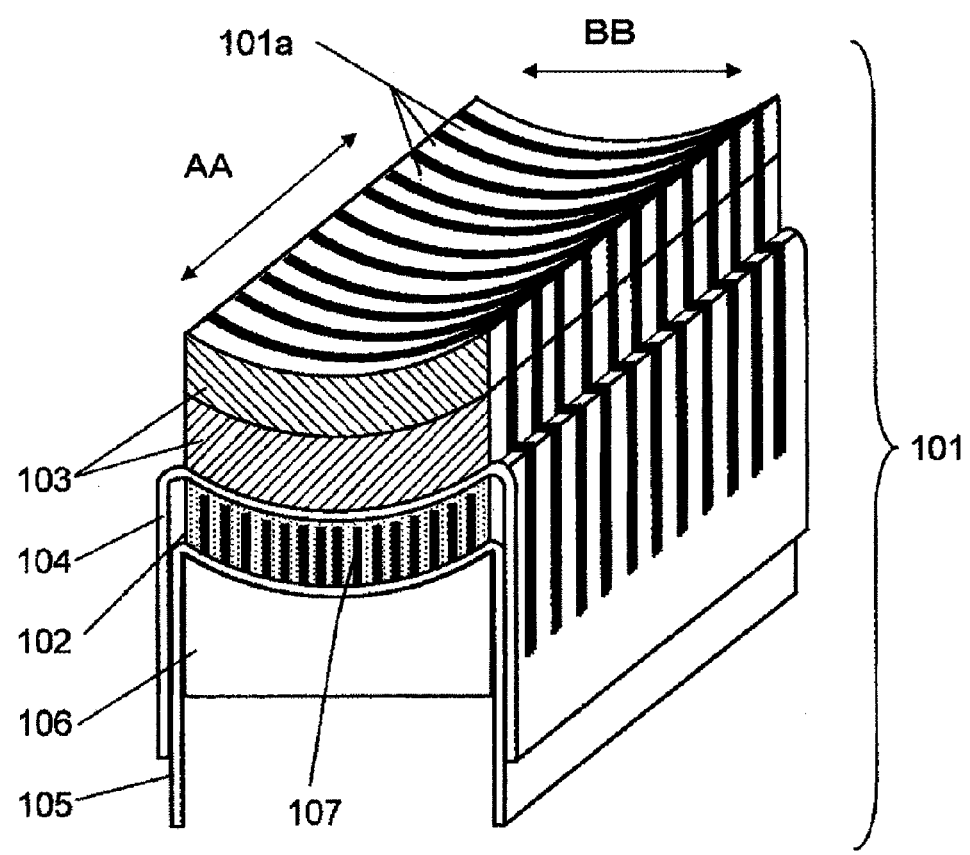
FIG. 13 A cross-sectional perspective view of a conventional array scanning type ultrasound probe.

The backing member 6 and the second signal flexible board 5 which have been given a desired curvature beforehand are bonded to the unit of FIG. 10 using an epoxy adhesive or the like to be stacked thereon, thus making the configuration of FIG. 9. At this time, it should be ensured that the incisions 16 are filled with the adhesive. At this time, since in the acoustic matching layer 15, the thickness from the incisions 16 to the surface of the acoustic matching layer 15, the surface not being in contact with the piezoelectric device 14, is as small as less than 1/9 of the wavelength, the unit of FIG. 10 is bonded to the backing member 6 and stacked thereon to follow the desired curvature given to the backing member 6 beforehand, thus being formed into a favorable shape. After that, division into several tens to several hundreds of elements is performed in the direction perpendicular to the array direction by means of cutting or the like. At this time, since the incisions 16 of FIG. 9 have an anchor effect to improve the adhesive strength of the unit of FIG. 9, division by cutting in the direction perpendicular to the array direction is favorably performed. FIG. 12 is a characteristic data view obtained by measuring the radius of curvature in direction BB from the surface on the first signal flexible board 4 side of FIG. 9 for different values of the dimension d shown in FIG. 9 or 11, and shows variations in the radius of curvature. Specifically, when a comparison is made among the one in which a thickness of 1/18 of the wavelength is left in the acoustic matching layer 15 by the incisions 16 from the surface of the acoustic matching layer 15, the surface not being in contact with the piezoelectric device 14, the one in which a thickness of 1/12 of the wavelength is left, and the one in which a thickness of 1/9 of the wavelength is left, the one in which a thickness of 1/9 of the wavelength is left has a very wide range of variations in the radius of curvature and a non-uniform ultrasound beam in direction BB, but the ones in which thicknesses less than that are left have favorable characteristics. In particular, it can be seen that the ones in which thicknesses less than 1/18 of the wavelength are left are excellent.

The above-described means prevents stress concentration at the piezoelectric device 14 from being caused by mechanically curving the unit of FIG. 10 so that the unit of FIG. 10 may have a curvature in the direction perpendicular to the array direction, prevents the damage of the piezoelectric device 14 from occurring, and makes it possible to favorably form a curvature in the direction perpendicular to the array direction.

It should be noted that though in this embodiment, the piezoelectric device 14 has the same length in the direction perpendicular to the array direction as components of the acoustic matching layer 15 and the backing member 6, similar effects are also exerted on a configuration in which the piezoelectric device 14 is shorter in length in the direction perpendicular to the array direction than components of the acoustic matching layer 15 and the backing member 6 in the case (see FIG. 5) where the incisions 16 are not provided in portions which are not in contact with the piezoelectric device 14 and the case (see FIG. 7) where the incisions 16 are provided therein.

It should be noted that this embodiment also has similar effects on an array type ultrasound probe with a linear shape and a convex type of array type ultrasound probe in the shape of a sector.

From the above, the use of the ultrasound probe of this embodiment can prevent a diminution of ultrasound at the time of transmission and at the time of reception due to the damage of a piezoelectric device. In other words, a sensitivity deterioration of a diagnostic image can be reduced. Further, an array scanning type ultrasound probe can be favorably formed to have a desired curvature.

INDUSTRIAL APPLICABILITY

As described above, the array scanning type ultrasound probe of this invention can prevent a diminution of ultrasound at the time of transmission and at the time of reception due to the damage of a piezoelectric device. Specifically, the array scanning type ultrasound probe of this invention has the effect of reducing a sensitivity deterioration of a diagnostic image, relates to an array scanning type ultrasound probe including a piezoelectric device, an acoustic matching layer, and a signal flexible board, and is useful as an array scanning type ultrasound probe or the like which can reduce characteristic deterioration of an array scanning type ultrasound probe due to the damage of a piezoelectric device.

The invention claimed is:

1. An ultrasound diagnostic equipment comprising: an ultrasound probe for transmitting and receiving ultrasound waves with respect to a test subject, and an ultrasound diagnostic equipment body for controlling the ultrasound probe by applying driving signals to the ultrasound probe, wherein the ultrasound probe comprises:
   an electroacoustic conversion unit formed by arranging a plurality of piezoelectric devices and a plurality of acoustic matching layers in a predetermined direction, each of the plurality of piezoelectric devices being an electroacoustic conversion device, the plurality of acoustic matching layers being respectively stacked on the plurality of piezoelectric devices; and
   a signal flexible board transferring electric signals to and from the plurality of piezoelectric devices for transmission and reception of ultrasound waves,
   wherein the signal flexible board is stacked on the plurality of acoustic matching layers
   wherein an incision passing through the plurality of piezoelectric devices in respective thickness directions of the piezoelectric devices and extending into the corresponding acoustic matching layers stacked on the respective piezoelectric devices is provided in parallel to the arrangement direction, and
   wherein the acoustic matching layers are longer in length in the direction perpendicular to the arrangement direction than the piezoelectric devices.

2. The ultrasound diagnostic equipment according to claim 1, wherein the incision is provided in plurality at regular intervals in a direction perpendicular to the arrangement direction.

3. The ultrasound diagnostic equipment according to claim 1, wherein in the acoustic matching layers stacked on the piezoelectric devices, an incision is provided in a portion of the acoustic matching layers, the portion protruding from the piezoelectric devices.

4. The ultrasound diagnostic equipment according to claim 1, wherein the incision in the acoustic matching layers is provided to have such a depth that the remaining acoustic matching layers have a dimension of less than ⅛ of a wavelength of ultrasound emitted by the piezoelectric devices.

5. The ultrasound diagnostic equipment according to claim 1, wherein each of the piezoelectric devices is divided into a respective plurality of piezoelectric elements by the incision passing therethrough, wherein the respective plurality of piezoelectric elements are electrically connected.

* * * * *